US006395961B1

(12) United States Patent
Petitte et al.

(10) Patent No.: US 6,395,961 B1
(45) Date of Patent: *May 28, 2002

(54) GENE TRANSFER IN CHICKENS BY INTRODUCTION OF DNA INTO MUSCLE IN OVO

(75) Inventors: James M. Petitte; Catherine A. Ricks; Patricia V. Phelps, all of Raleigh; Christopher Williams, Apex, all of NC (US)

(73) Assignee: North Carolina State University, Raleigh, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/096,945

(22) Filed: Jun. 12, 1998

Related U.S. Application Data

(63) Continuation of application No. 08/383,703, filed on Feb. 1, 1995, now Pat. No. 5,784,992, which is a continuation of application No. 07/999,399, filed on Jan. 21, 1993, now abandoned, which is a continuation-in-part of application No. 07/826,030, filed on Jan. 27, 1992, now abandoned.

(51) Int. Cl.[7] .................... C12N 15/00; A01K 48/00; A01K 45/00; A01K 67/027
(52) U.S. Cl. .................... 800/21; 800/19; 800/23; 514/44; 119/6.8
(58) Field of Search .................... 514/44; 800/21, 800/23; 424/93.6

(56) References Cited

U.S. PATENT DOCUMENTS 5,162,215 A    11/1992   Bosselman et al.

FOREIGN PATENT DOCUMENTS

| GB | 2223755 A | 9/1988 |
| WO | WO 90/03439 | 4/1990 |
| WO | WO90/11092 | 10/1990 |

OTHER PUBLICATIONS

Verma et al., Gene therapy–promises, problems and prospects, 1997, Nature, vol. 389, pp. 239–242.*
Ross et al., Gene therapy in the United States: a five year status report, 1996, Human Gene Therapy, vol. 7, pp. 1781–1790.*
Souza et al. Expt. Zool., vol. 232, pp. 465–473, 1984.*
Antin et al. Devel. Biol., vol. 143, pp. 122–129, 1991.*
Nabel et al. Science, vol. 247, pp. 1285–1288, Sep. 14, 1990.*
Verma Nature, vol. 289, pp. 239–241, Sep. 1997.*
Ross Human Gene Therapy, vol. 7, pp. 1781–1790, Sep. 1996.*
Al Moustafa et al.; "Targets of v–myc tumorigenesis in the avian embryo depend on time and not on site of retroviral infection, " *Cell Differentiation and Development* 25:119–134 (1988).
Chen et al.; "Vectors, promoters, and expression of genese in chick embryos," *J. Reprod. Fert. Suppl.* 41:173–182 (1990).
Demeneix et al.; "Gene transfer into intact vertebrate embryos," *Int. J. Dev. Biol.* 35:4481–484 (1991).
Yuko Ando et al., *Ultrastructural Evidence that Chick Primordial Germ Cells Leave the Blood–Vascular System Prior to Migrating to the Gonadal Anlagen,* Develop., Growth and Differ., 25:345–352 (1983).
Robert A. Bosselman et al., *Germline Transmission of Exogenous Genes in the Chicken,* Science, 243:533–535 (1989).
C.L. Brazolot et al., *Efficient Transfection of Chicken Cells by Lipofection, and Introduction of Transfected Blastodermal Cells Into the Embryo,* Molecular Reproduction and Development, 30:304–312 (1991).
Andy Coghlan, New Scientist 19 (Oct. 31, 1992).
Elisabeth Dupin, *Cell Division in the Ciliar Ganglion of Quail Embroys in Situ and after Back–Transplantation into the Neural Crest Migration Pathways of Chick Embryos,* Developmental Biology, 105:288–299 (1984).
R.S. Goldstein et al., *The Microenvironment Created by Grafting Rostral Half–Somites is Mitogenic for Neural Crest Cells,* Proc. Natl.Acad. Sci., 87:4476–4480 (1990).
M. Bagnall et al., *The Contribution Made by Cells from a Single Somite to Tissues Within a Body Segment and Assessment of their Integration with Similar Cells from Adjacent Segments,* Development, 107:931–943 (1989).
E.G. Nabel, *Site–Specific Gene Expression in Vivo by Direct Gene Transfer into the Arterial Wall,* Science, 249:1285–1288.
D.W. Salter et al, *Transgenic Chickens; Insertion of Retroviral Genes into the Chicken Germ Line,* Virology, 157:236–240 (1987).
D.W. Salter et al., *Gene Insertion into the Chicken Germ Line by Retroviruses,* Symposium, 1445–1458 (1985).

(List continued on next page.)

Primary Examiner—Michael C. Wilson
(74) Attorney, Agent, or Firm—Myers Bigel Sibley & Sajovec

(57) ABSTRACT

A method of altering the phenotype of a bird comprises introducing a DNA molecule into the muscle tissue of a bird contained within an egg during in ovo incubation. The DNA molecule is selected to be effective to cause a change in phenotype, such as an increase in growth rate, feed efficiency, immune response, or a combination of these and other phenotypes in the bird after hatch. A DNA molecule may further be selected to increase disease resistance, induce disease prevention, or neutralize maternal antibodies by the expression of an antigen over a period of time.

19 Claims, 1 Drawing Sheet

OTHER PUBLICATIONS

R.M. Shuman et al., *Gene Transfer by Avian Retroviruses*, Symposium, 1437–1444 (1985).

K. Simkiss et al., *Transfer of Promordial Germ Cell DNA Between Embryos*, Protoplasma, 151:164–166 (1989).

L.M. Souza et al, *Application of Recombinant DNA Technologies to Studies on Chicken Growth Hormone*, The Journal of Experimental Zoology, 232:465–473 (1984).

B.C. Wentworth et al., *Manipulation of Avian Primordial Germ Cells and Gonadal Differentiation*, Poultry Science Assoc., 999–1010 (1989).

J.A. Wolff et al., *Direct Gene Transfer into Mnouse Muscle in Vivo*, Science, 247:1465–1468 (1990).

Hua Lin et al., *Expression of Recombinant Genes in Myocardium in Vivo After Direct Injection of DNA*, Circulation 82:2217–2221 (1990).

P.B. Antin et al., *Transgene Expression in theQM Myogenic Cell Line*, Development Biology, 143:122–129 (1991).

Thesis of F. Flamant, *Utilisation de vecteurs dérivés du virus de l'Erythroblastose aviaire (AEV) pour le transfert de génes chez les embryons de poulet*, pp. 14–34, Figs. 15 & 16 (1996).

* cited by examiner

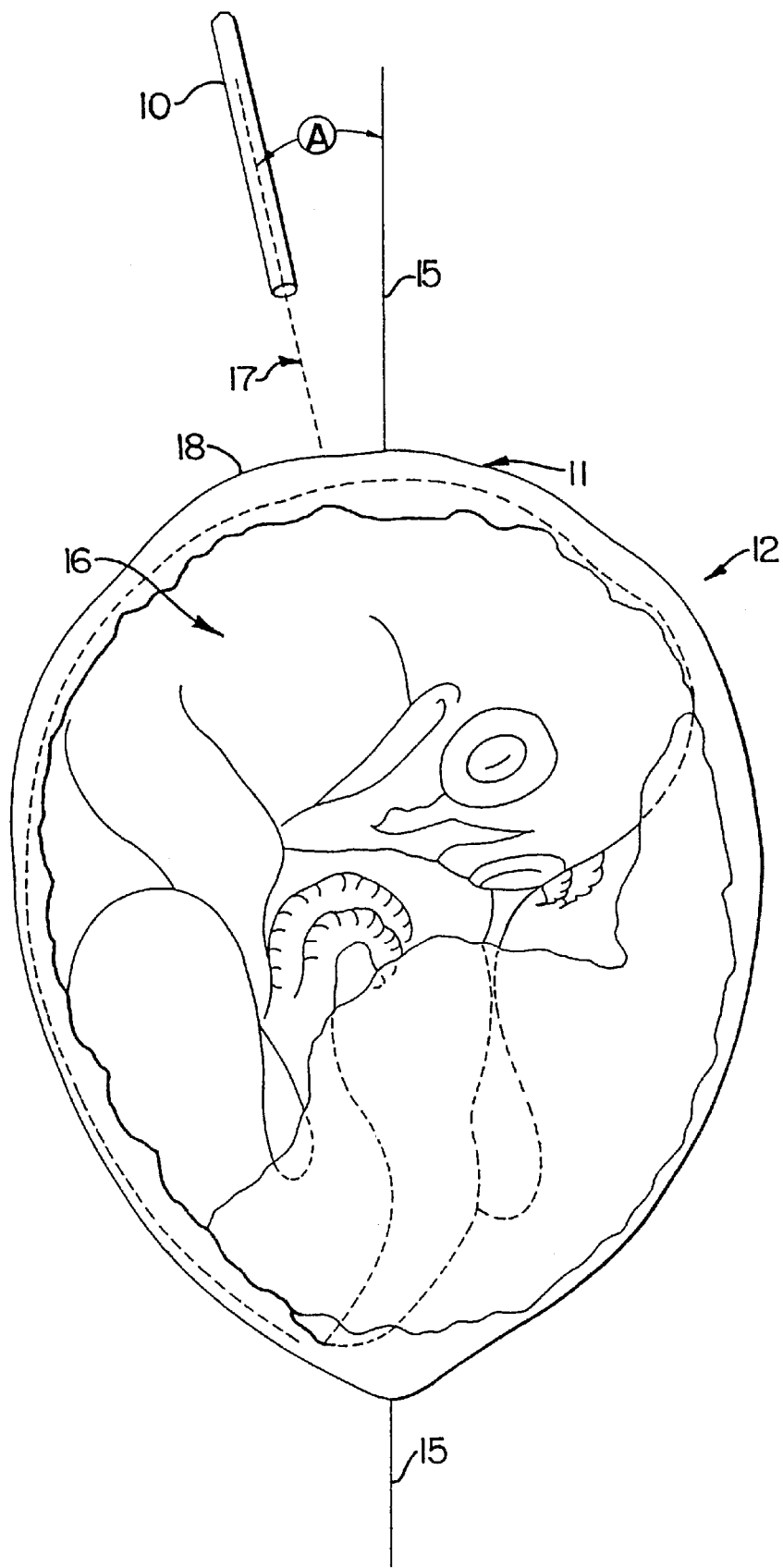

GENE TRANSFER IN CHICKENS BY INTRODUCTION OF DNA INTO MUSCLE IN OVO

RELATED APPLICATIONS

This application is a continuation of U.S. patent application Ser. No. 08/383,703, filed Feb. 1, 1995, now U.S. Pat. No. 5,784,992, which is a continuation of U.S. patent application Ser. No. 07/999,399, filed Jan. 21, 1993, now abandoned, which is a continuation-in-part of U.S. patent application Ser. No. 07/826,030, filed Jan. 27, 1992, now abandoned, the contents of which are herein incorporated by reference in their entirety.

FIELD OF THE INVENTION

This invention relates to the methods of altering the phenotype of birds by introducing foreign DNA into the muscle of birds.

BACKGROUND OF THE INVENTION

Commercial poultry is an extremely important source of food. However, there has been comparatively little attention given to methods of producing useful changes in the phenotype of birds through genetic engineering techniques. This is unfortunate, because such techniques offer a much more rapid technique for introducing desirable phenotypic traits into birds than classical breeding techniques.

Currently, the most widely investigated method of gene transfection in poultry employs retroviral vectors. Exemplary is Souza et al., *J. Exptl. Zool.* 232, 465–473 (1984), in which a retroviral vector encoding growth hormone was injected into the vascularized portion of the yolk sac of 9 day old embryos. See also Shuman and Shoffer, *Poult. Sci.* 65, 1437–1444 (1986); Salter et al., *Poultry Sci.* 65, 1445–1468 (1986); Salter et al., *Virology* 157, 236–240 (1987); Bosselman et al., *Science* 243, 533–535 (1989); and U.S. Pat. No. 5,162,215 to Bosselman et al.

Nabel et al., *Science* 249 1285–1288 (1990), and Wolff et al., *Science* 247, 1445–1468 (1990), state that transient expression of 2–5 months may be obtained from direct microinjection of DNA, but do not suggest how these techniques may be applied to genetically engineering poultry. Nabel et al. note that the expression of DNA encoding β-galactosidase injected into porcine arterial segments was limited to the microinjection site. Acsadi et al., *New Biologist* 3, 71–81 (1991) state that myocardial cells were able to transiently express injected foreign genes.

Simkiss et al., *Protoplasma* 151, 164–166 (1989) indicate that primordial germ cells of Stage XVII embryos containing endogenous retroviral sequences can be transferred to comparable recipient Stage XVI embryos that lack the retroviral marker by cardiac puncture. At day 17 of incubation, dot blots on recipient birds showed donor DNA to be present in the gonads, and traces of donor DNA to be present in the liver and heart tissues. The expression of the injected DNA molecules was not reported.

PCT patent application Ser. No. US90/01515 discloses a method of delivering a nucleic acid sequence to the interior of a vertebrate cell. Injection of a DNA molecule into poultry was not reported.

In view of the foregoing, an object of the present invention is to provide methods of changing the phenotype of birds through genetic engineering procedures.

An additional object of the present invention is to provide a method of changing the phenotype of birds in which expression of an exogenous DNA sequence is sufficient produce the phenotypic change.

Another object of the present invention is to provide a method of changing the phenotype of birds which is rapid and convenient.

SUMMARY OF THE INVENTION

A first aspect of the present invention is a method of altering the phenotype of a bird. The method comprises introducing a DNA molecule into the cells of a bird contained within an egg during in ovo incubation, with the DNA molecule being effective to cause a change in phenotype in the bird after hatch (e.g., a change in growth rate, feed efficiency, disease resistance, or a combination of all of these factors). Introduction of the DNA may be carried out by any suitable means, including injecting the DNA molecule in ovo into any compartment of the egg including the body of the embryo.

Preferably, the egg into which the DNA is introduced is incubated to hatch, and the bird so produced raised to at least an age at which the change in phenotype is expressed.

A second aspect of the present invention is a bird produced by the foregoing methods.

In an illustrative embodiment of the foregoing, the DNA molecule is introduced into muscle tissue of the bird in ovo, preferably by direct microinjection during late embryonic development.

A third aspect of the present invention is a method for altering the phenotype of a bird comprising introducing a DNA molecule into the muscle tissue of a bird contained within an egg during in ovo incubation, wherein the DNA molecule is effective in causing a change in phenotype in the bird after hatch.

A fourth aspect of the present invention is a method for immunizing a bird comprising introducing a DNA molecule into the muscle tissue of a bird contained within in an egg during in ovo incubation, wherein the DNA molecule is effective in inducing an immune response in the bird.

A fifth aspect of the present invention is a method for treating a bird comprising introducing a DNA molecule encoding for an antigen into the muscle tissue of a bird contained within an egg during in ovo incubation in an amount sufficient to neutralize maternal antibodies. In a preferred embodiment, the DNA molecule is introduced at or after the development of immunocompetence by the bird.

A sixth aspect of the present invention is the use of a DNA molecule for the preparation of a medicament for carrying out any of the foregoing methods.

A seventh aspect of the present invention is an apparatus for the introduction of a DNA molecule in an egg during in ovo incubation for carrying out any of the foregoing methods.

BRIEF DESCRIPTION OF THE DRAWINGS

The FIGURE illustrates a particular method and apparatus for introducing substances into the muscle of birds in ovo.

DETAILED DESCRIPTION OF THE INVENTION

There are several aspects of avian embryonic development which make it an attractive target for somatic cell gene transfer. First, since the greatest period of embryonic development occurs in the egg outside the maternal reproductive tract, the embryo can be easily accessed for the introduction of exogenous DNA.

Second, the fact that the egg is a multi-compartmentalized unit can be exploited to deliver biological materials to specific embryonic sites. For example, the yolk sac in the early embryo functions to manufacture blood. Immediately prior to hatching, the yolk sac serves a primarily nutritional function and is taken into the intestinal tract and thereby transported to the cecal pouches during and after hatch. Therefore, yolk sac administration of materials can lead to both embryonic cecal or vascular system delivery. Vascular system delivery through administration of DNA into the yolk sac would be particularly desirable for administering DNA constructs capable of expressing physiologically active peptides in the bird, such as growth hormone, lymphokines such as interferon and interleukin-2, insulin-like growth factor, or thyroid releasing hormone (TRH). In addition, administration of a peptide or DNA construct can be efficiently carried out by injection of the molecule onto the chorio-allantoic membrane or onto the air cell membrane. Finally, access to the embryonic musculature compartment can be achieved by direct embryonic injection at transfer in the last quarter of incubation, and in chickens more preferably, preferably in days 17–19 of incubation.

Third, it is of no deleterious consequence if the transformed embryo and chicken is chimeric, so long as a physiological response is achieved in the animal after hatch sufficient to evoke the phenotypic change sought.

The foregoing and other aspects of the present invention are explained in greater detail below.

A. Phenotypic Alteration

The present invention provides a number of methods of altering the phenotype of a bird after hatch by in ovo introduction of a DNA molecule to the bird. As used herein, an altered "phenotype" of a bird is intended to encompass a sustained alteration in the cellular biochemistry of a bird by the expression of a foreign DNA molecule within the tissues of the bird, which alteration results in a change in one or more physical characteristics of the bird. Thus under this definition an altered phenotype can be a change in size, appearance, endocrine response growth rate, immune response to specific antigens, metabolic rate, feed consumption and efficiency, gender, and the like. Alternatively stated, the present invention provides methods for inducing a physiological response (e.g., an immune response, or a hormonal or endocrine response) in a bird after hatch through administering to a bird in ovo a DNA molecule encoding and expressing a peptide, which DNA molecule is administered in an amount effective to induce said physiological response after hatch. Note that the physiological response may be directly induced after hatch, or may be indirectly induced after hatch (such as by induction of a physiological response prior to hatch which endures after hatch.

A particular altered phenotype of interest is a change in immune response wherein introduction of a DNA molecule immunizes the bird. Exemplary DNA molecules for introduction are those that encode a protective antigenic protein that induces an immune response from the recipient bird. This can be done in combination with or, more preferably, in lieu of, vaccination of the bird to protect against a specific pathogen.

Altering the endogenous immune response of a bird in ovo is of particular interest due to the presence of maternal antibodies in embryonic and young mammals and birds. Maternal antibodies can interfere with typical vaccination programs for these animals. These antibodies, provided to the neonate from the bloodstream of the mother, conjugate with specific antigens and thus provide natural protection against those antigens prior to the development of immunocompetence by the neonate.

Unfortunately, maternal antibodies can also hinder typical Vaccination protocols; they bind to the immunogenic component of the vaccine and thus inhibit neonatal production of antibodies. The presence of maternal antibodies precludes vaccination early in the development of the neonate. Typically, multiple vaccination protocols are required so that active immunization can occur once maternal antibody levels have decreased to a sufficiently low level that they will no longer interfere with the vaccine.

The present invention provides a novel strategy for counteracting maternal antibody interference with vaccination. One aspect of this invention is a method of immunizing a bird comprising introducing a DNA molecule that encodes an antigen into the muscle tissue of a bird contained within an egg in ovo in an amount sufficient to neutralize maternal antibodies. Once neutralized, the maternal antibodies no longer interfere with a vaccine containing the antigen: thus such a vaccine can be used to immunize the bird. Alternatively, the DNA molecule can be introduced in an amount effective so that, upon expression, not only does the antigen neutralize maternal antibodies, but also provides an immunogen which vaccinates the bird against a specific pathogen.

The DNA molecule introduced can be any molecule that encodes an antigen that will neutralize maternal antibodies present in the bird. Exemplary antigens of interest include those produced by Gumboro Disease virus, Newcastle Disease Virus (NDV), Infectious Bursal Disease Virus (IBDV), Rous sarcoma virus, *E. coli*, and coccidia.

The DNA molecule can be introduced by any of the methods set forth in Section C below, and can comprise any of the DNA construct configurations set forth below.

It is preferred that the DNA molecule be introduced so that the antigen is expressed as or after the embryo develops immunocompetence, which is generally in the last quarter of incubation. At immunocompetence, surface antigens encoded by the DNA construct can stimulate both a B- and T-cell response, resulting in immunization before challenge by pathogens encountered in the field after hatch. The timing and the duration of the last quarter of incubation varies among different avian species due to the variation in incubation duration. For example, for chickens, the last quarter of incubation is from about day 16 to hatch; for turkeys, the last quarter is from about day 19 to hatch.

B. Subjects and Time of Administration

The present invention may be carried out on any avian subject, including, but not limited to, chickens, turkeys, ducks, geese, quail, and pheasant. The DNA may be introduced in ovo at any time during incubation, the duration of which will vary depending upon the species. For example, DNA may be introduced into chicken eggs early in incubation (e.g., between about days 2 and 3 of incubation) or late in incubation (e.g., during the last quarter of incubation; i.e., between about 16 and 21 days of incubation).

The DNA molecule may be introduced into any region of the egg, including the air cell, the albumen, the chorio-allantoic membrane, the yolk sac, the yolk, the allantois, the amnion, or directly into the embryonic bird. In a preferred embodiment of the invention, the DNA molecule is introduced into muscle tissue of the embryonic bird, and in a more preferred embodiment, the DNA molecule is introduced into skeletal muscle tissue. Introduction of a DNA molecule encoding a protein which remains within the muscle cell can be used to administer a foreign protein directly and specifically to muscle cells. Alternatively, a DNA molecule can be introduced which encodes a protein which will be secreted from the muscle cell; this method can be used to deliver a protein to the entire body of the bird through contact between the muscle tissue and plasma. Exemplary skeletal muscle tissue introduction sites are breast muscle and pipping muscle tissue, which are located near the eggshell and thus are relatively easily reached by injection apparatus without damage to other embryonic structures.

C. DNA Constructs

The DNA molecule introduced in ovo is, in general, a construct comprising of a promoter functional in avian cells and a gene encoding a peptide or protein operably linked to the promoter. Preferably, the protein or peptide is physiologically active and capable of producing a phenotypic change in the bird. In general, the DNA construct may be a linear DNA molecule or a molecule carried by a vector or other suitable carrier such as liposomes, calcium phosphate, or DMSO. Vectors, as discussed below, may be plasmids, viruses (including retroviruses), and phage, whether in native form or derivatives thereof. The DNA molecule preferably should not contain retroviral DNA portions sufficient for integration of the infecting DNA into the chromosomal DNA of the host bird.

Illustrative of genes encoding a protein or peptide are those which encode a protein or peptide selected from the group consisting of growth hormone, thyroid releasing hormone (TRH), epidermal growth factor, and immunogenic recombinant antigens such as those produced by Marok's Disease Virus, Infectious Bronchitis Virus, mycoplasma, Avian Leucosis Virus, reovirus, Pox Virus, Adenovirus, cryptosporidia, chicken anemia agent, Pasteurella species, avian influenza virus, Marek's MDX, Gumboro Disease virus, Newcastle Disease Virus (NDV), Infectious Bursal Disease Virus (IBDV), Rous sarcoma virus, *Echerichia coli*, and Eimeria species such as *Eimeria tenella* (causing coccidiosis).

The production of cloned genes, recombinant DNA, vectors, transformed host cells, proteins and protein fragments by genetic engineering is well known.

See e.g., U.S. Pat. No. 4,761,371 to Bell et al. at Col. 6 line 3 to Col 9 line 65; U.S. Pat. No. 4,877,729 to Clark et al. at Col. 4 line 38 to Col 7 line 6; U.S. Pat. No. 4,912,038 to Schilling at Col. 3 line 26 to Col. 14 line 12 (applicants specifically intend that the disclosure of these and all other patent references cited herein be incorporated herein by reference). Protocols for restriction endonuclease digestion, preparation of vectors, DNA purification and other such procedures were essentially as described in standard cloning manuals. See Sambrook et al., *Molecular Cloning. a Laboratory Manual*, (2d Ed., Cold Spring Harbor Press, New York (1989)).

A vector is a replicable DNA construct used to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription, enhancer elements which can stimulate transcription manyfold from linked heterologous promoters, a splice acceptor and/or donor molecules, and termination and polyadenylation signals. Also required is a DNA sequence for a ribosome binding site capable of permitting translation which is operably linked to the gene to be expressed.

Recently, a muscle-specific promoter has been isolated which is positioned upstream of both the skeletal muscle structural gene and the essential proximal promoter element and is operably associated with each. (Mar and Ordahl *Proc. Natl. Acad. Sci. USA* 85, 6404–6408 (1988)). Other exemplary promoters suitable for use in skeletal muscle include promoters associated with the genes expressing skeletal actin, phosphoglycerate kinase (PGK), dihydrofolate reductase (DHFR), muscle creatinine kinase, and fibroblast growth factor, the promoter for Herpes Virus, thymidine kinase, and promoters for viral long-terminus repeats, such as Rous Sarcoma Virus.

Vectors comprise plasmids, viruses (e.g. adenovirus, cytomegalovirus), phage, and DNA fragments integratable into the host genome by recombination. The vector replicates and functions independently of the host genome.

D. Gene Targeting

Direct DNA microinjection has been used successfully for laboratory animals such as the mouse, and for large animals such as domestic cattle, sheep, and pigs by injecting small volumes of DNA solutions into the pronuclei of newly fertilized ova. Use of this system in poultry, however, has been limited to the newly fertilized egg (before oviposition) and involves an in vitro culture system using a combination of shell-less culture with surrogate-eggshell culture (Rowlett and A Simkiss, *Brit. Poult. Sci.* 28, 91–101 (1987); Perry, *Nature* 331, 70–72 (1988); Naito et al., *J. Exptl. Zool.* 254, 322–326 (1990)). This has allowed the microinjection of DNA into the cytoplasm of the avian egg at about the time of the first cleavage divisions and has yielded transient expression in the embryo (Sang and Perry, *Mol. Reprod. and Dev.* 1, 98–106 (1989)).

In the present invention, the DNA is injected or deposited directly into muscle tissue in the avian embryo. By "muscle tissue" is meant skeletal muscle tissue, such as the breast muscle or muscle in the shoulder of the embryonic bird. The DNA may be deposited in the muscle tissue by any suitable means, as discussed below. The DNA is typically deposited by inserting a hollow syringe or needle into the muscle tissue and injecting an aqueous pharmaceutically acceptable carrier solution containing the DNA into the muscle tissue, as discussed in greater detail below. Injecting of the solution may be carried out before withdrawing the needle from the muscle tissue or coincurrently with withdrawing the needle from the muscle tissue. In the embodiment discussed below, injection is carried out by inserting the needle into and through the muscle tissue and the liquid discharged through the needle concurrently with withdrawing the needle through the muscle tissue, whereby DNA is deposited along the entire path of needle withdrawal in the muscle tissue.

E. Methods of Introducing DNA into Eggs

Any suitable means may be used for introducing the DNA in ovo, including in ovo injection, high pressure spray through the egg shell, and ballistic bombardment of the egg with microparticles carrying the DNA construct. Preferably, the DNA is deposited by depositing an aqueous, pharmaceutically acceptable solution in the muscle, which solution contains the DNA to be deposited.

Where in ovo injection is used the mechanism of injection is not critical, but it is preferred that the method not unduly damage the tissues and organs of the embryo or the extra embryonic membranes surrounding it so that the treatment will not decrease hatch rate. A preferred injection site is muscle tissue, particularly skeletal muscle, and more particularly breast muscle and pipping muscle tissue, which are located near the eggshell and thus are relatively easily reached by injection apparatus without damage to other embryonic structures and without compromising the protection afforded by the eggshell. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being the EMBREX INOVOJECT™ system (described in U.S. Pat. No. 4,681,063 to Hebrank), and U.S. Pat. Nos. 4,040,388, 4,469,047, and 4,593,646 to Miller. The disclosure of these references and all references cited herein are to be incorporated herein by reference. All such devices, as adapted for practicing the present invention, comprise an injector Containing the DNA as described herein, with the injector positioned to inject an egg carried by the apparatus with the DNA. In addition, a sealing apparatus operatively associated with the injection apparatus may be provided for sealing the hole in the egg after injection thereof.

The currently preferred apparatus for practicing the present invention is disclosed in U.S. Pat. No. 4,681,063 to Habrank and U.S. Pat. No. 4,903,625 to Hebrank, the disclosure of which are incorporated herein by reference. This device comprises an injection apparatus for delivering fluid substances into a plurality of eggs and suction apparatus which simultaneously engages and lifts a plurality of individual eggs from their upwardly facing portions and cooperates with the injector for injecting the eggs while the eggs are engaged by the suction apparatus. The features of this apparatus may be combined with the features of the apparatus described above for practicing the present invention. Those skilled in the art will appreciate that this device can be adapted for injection into any portion of the egg by adjusting the penetration depth of the injector, as discussed in greater detail below.

A particularly preferred embodiment of an injection method and apparatus is schematically illustrated by the FIGURE. The method and apparatus is essentially as described above, but involve positioning an elongate injector or injection needle 10 at the large end 11 of the egg 12 at an angle (A) offset from the long axis 15 of said egg, the angle selected so that the needle is directed toward the shoulder or breast of said embryo 16. The needle is then inserted through the shell of the egg, along an essentially linear path of travel 17, to a depth sufficient to pass into the shoulder or breast of the embryo. The substance to be deposited in the egg, which may be either a liquid or a syringable solid (but is preferably an aqueous solution containing the DNA as described above), is then injected through the needle. In a preferred embodiment, the needle is withdrawn along the essentially linear path of travel, and the step of injecting the substance is carried out concurrently with the step of withdrawing the needle so that the substance is administered along the path of travel within the egg. The angle of offset (A) is sufficient to enhance the probability of injecting into shoulder or breast muscle. Typically, the angle is 1 to 5 degrees, and preferably the angle is from 2 to 3 degrees. The needle may be inserted to a depth sufficient beneath the egg shell 18 to pass into or pass into and through the shoulder or breast of the embryo; typically, the needle is inserted ⅞ inches into the egg. The apparatus may be modified to include means operably associated with the apparatus for positioning the egg at an angle with respect to the needle to achieve said angle (A), such as by mounting and positioning the needles at an angle with respect to the suction apparatus.

The present invention is explained further in the following non-limiting examples. In these Examples, "$\mu L$" means microliters, "$\mu g$" means micrograms, "mL" means milliliters, "cc" means cubic centimeters, "mm" means millimeters, "mM" means concentration in millimoles, "mg" means milligrams, and "C" means degrees Celsius.

EXAMPLE 1

Injection of DNA In Ovo

Using the Embrex Inovoject™ system described above, gene transfer is accomplished by injecting 25, 50, or 100 $\mu g$ of pmiwZ or pRSV-ADH DNA in 100 $\mu L$ of phosphate buffered saline (PBS) into the embryo in the region defined by the amnion at day 18 of incubation. Embryos are sacrificed at 19, 20, or 21 days of incubation and muscle tissue is examined histologically for construct expression. LacZ expression is examined in living tissue using a non-toxic fluorescent substrate (ImaGene™, Molecular Probes, Inc.) or in fixed tissue using X-gal (Ueno et al., *Develop. Growth and Differ*. 30(1), 61–73 (1987)). ADH expression is examined in fixed tissues using 2-butanol (Ordahl, supra (1986)), a substrate which is specific for Drosophila ADH and cannot be used by vertebrate ADH. Therefore, endogenous expression is able to be distinguished from erogenous expression.

When a construct is expressed, the other injected embryos are allowed to hatch and are raised to 1–2 weeks of age. At various points during this time, the birds are sacrificed and the portion of muscle corresponding to the site of injection and expression in the 19–21 day embryos is analyzed for bacterial β-galactosidase or Drosophila ADH activity.

EXAMPLE 2

Preparation and Injection of Plasmids into Muscle Tissue

Two plasmid constructs, pmiwz and pRSV-LUX, were used to evaluate gene transfer into muscle tissue. Plasmid pmiwz consists of an *E. coli* β-galactosidase reporter gene, a chicken a-crystalline enhancer, and a Rous Sarcoma Virus (RSV) promoter. This construct was chosen to take advantage of the fact that the enhancer and promoter are active in muscle, and the histochemical assay for β-galactosidase is easy to perform. However, the histochemical staining for β-galactosidase is a qualitative assay. A second construct, the PRSV-LUX plasmid, was chosen to provide a quantitative assay for gene expression, and to demonstrate that expression of injected DNA in muscle is not specific to one particular plasmid construct. This plasmid contains a firefly luciferase reporter gene and an RSV promoter. Expression of the gene product encoded by the pRSV-LUX plasmid may be quantitatively measured by a biochemical assay that measures the luminescence generated by the luciferase enzyme.

Plasmid DNA was purified in a covalently closed circular form. Solutions to be injected consisted of 250, 500, 750 or 1000 $\mu g/mL$ of DNA, and 50 $\mu L/mL$ of India Ink in Phosphate Buffered Saline (PBS). India ink was used to mark the precise site of injection at necropsy; it was not metabolized and thus persisted for at least two weeks in the muscle. Each chick was injected at hatch in the back portion of the thigh muscle with 100 $\mu L$ of the appropriate dilution of DNA. Injection was carries out with a 1 cc syringe with a 26 G ⅜ inch needle which was collared so that the needle penetrated 2 mm into the muscle. The DNA solution was delivered as the leg muscle was gently squeezed to ensure accurate placement of the needle. Chicks were then placed in pens for one or two weeks before being euthanized with $CO_2$.

EXAMPLE 3

Detection of DNA Constructs in Muscle Tissue by Polymerase Chain Reaction

Uptake of plasmid DNA by the muscle and persistence of the DNA molecules was measured at one week post-injection by a Polymerase Chain Reaction (PCR)-based procedure. To obtain DNA samples from muscle for analysis by PCR, muscle surrounding the site of injection was excised and placed in a buffer consisting of 50 mM Tris pH8.0, 100 mM EDTA pH8.0, 100 mM NaCl, 1% SDS, and 0.5 mg/ml proteinase K. After incubation overnight at 55° C., the samples were extracted once with an equal volume of phenol, once with an equal volume of a phenol:chloroform solution (50:50), and once with an equal volume of chloroform, then were precipitated in sodium acetate and ethanol. The DNA was resuspended in 10 mM Tris pH 8.0, 1 mM EDTA pH 8.0, and the concentration was determined. DNA samples were then subjected to the PCR following standard techniques using oligonucleotide primers specific for the E. coli β-galactosidase. PCR products were examined by gel electrophoresis to determine the presence or absence of the injected plasmid DNA molecules.

EXAMPLE 4

Results of PCR Assay on β-Galactosidase Persistence in Muscle Tissue

The procedure described in Example 3 produced the data shown in Table 1 below.

TABLE 1

| pmiwZ Present in One-Week Old Birds | | | | | |
|---|---|---|---|---|---|
| DNA dosage (μg) | 0 | 25 | 50 | 75 | 100 |
| Total birds tested | 4 | 6 | 5 | 5 | 1 |
| Positive samples | 0 | 6 | 5 | 4 | 1 |

Table 1 shows that at all dosages of pmiwz tested, PCR indicates that the plasmid persists in the muscle tissue proximate to the injection site.

Thus these data show that the DNA construct injected into the muscle tissue is capable of residing therein for at least one week. Also, these results indicate that there are no nucleases present in the muscle tissue of the newly hatched bird that preclude the maintenance of the DNA construct.

EXAMPLE 5

Detection of β-Galactosidase in Muscle Tissue

Muscle tissue was obtained for histochemical staining for the detection of β-galactosidase activity at 4, 6, 7 and 14 days after injection of pmiwz. Birds were euthanized by $CO_2$ and skin overlaying the site of injection was removed. A muscle clamp was positioned around the site of injection (identified by the presence of India ink staining) and the muscle was trimmed around the clamp to free the sample from the surrounding tissues. The clamped muscle was placed on a cheesecloth saturated with PBS and held at room temperature for 5 minutes. The muscle was then removed from the muscle clamp and frozen in isopentane cooled with liquid nitrogen.

Frozen sections were prepared on gelatin-coated slides. Slides were fixed for 10 minutes at room temperature in 0.05M phosphate buffer pH 7.4, 0.2% glutaraldehyde, 2% formaldehyde and 2 mM $MgCl_2$. The slides were removed from the fixative and rinsed three times for twenty minutes each in a solution of 0.05 M phosphate buffer pH 7.4, 2 mM $MgCl_2$ and 0.02% NP-40. Slides were then stained overnight in darkness in a solution of 0.05 M phosphate buffer pH 7.4, 0.5 mg/mL X-gal, 5 mM potassium ferricyanide, 5 mM potassium ferrocyanide, and 2 mM $MgCl_2$.

After staining, the slides were rinsed in distilled water and air-dried. Cells containing an active E. Coil β-galactosidase protein stained blue. By maintaining the fixative and staining solutions at pH 7.4, background staining of endogenous chicken galactosidase is eliminated.

EXAMPLE 6

Results of μ-Galactosidase Staining Assay

Muscle biopsies according to the methods of Example 6 were performed and histochemically analyzed for the E. coli β-galactosidase protein. The results are shown below in Table 2.

TABLE 2

| Detection of β-Galactosidase 6 days posthatch | | | | | |
|---|---|---|---|---|---|
| DNA dosage (μg) | 0 | 25 | 50 | 75 | 100 |
| Total Birds Tested | 2 | 2 | 2 | 1 | 1 |
| Positive samples | 0 | 2 | 2 | 1 | 1 |

These results demonstrate that injected DNA is capable of expressing active protein in chick muscle up to 10 days post-injection.

These data indicate that endogenous nucleases and proteases present in the bird did not block the expression of the pmiwz construct.

EXAMPLE 7

Detection of Luciferase Activity

To avoid the need for precise identification of injection site, a construct encoding the firefly luciferase gene, PRSV-LUX was injected; the luminescent signal produced by this enzyme is detectable in relatively low concentrations, which permits the inclusion of large amounts of muscle tissue in samples to ensure that the injection site is included in the sample. Zero, 25 and 50 μg of this construct were injected into muscle at day of hatch; muscle was harvested one week post-injection.

To determine levels of luciferase activity in injected muscle, muscle samples were harvested after euthanasia of chickens and immediately frozen in liquid nitrogen. Samples were ground in a dry-ice cooled mortar and pestle to a fine powder, resuspended in a lysis buffer, and incubated at room temperature for 15 minutes. The extract was then subjected to three freeze-thaw cycles, and centrifuged at 14,000×g for 3 minutes. The pellet was resuspended in fresh lysis buffer, and the procedure was repeated as above. Both supernatants were pooled and frozen at −70° C. Samples were then assayed for luciferase activity using a commercially available assay system (Promega).

EXAMPLE 8

Results of Luciferase Activity Assay

After injection according to the procedure of Example 2 and preparation of samples as described in Example 7, samples were analyzed for luciferase activity as measured in light units of luminescence produced. The results are shown below in Table 3.

TABLE 3

| Luceriferase Activity Assay | | | |
|---|---|---|---|
| DNA dosage (µg) | 0 | 25 | 50 |
| Total birds tested | 7 | 7 | 6 |
| Positive samples | 0 | 4 | 4 |
| Luminescence (Average light units) | 0 | 0.18 | 0.26 |

These data provide confirmation of the data of Example 8 that indicate the expression of protein by the injected DNA construct. These data further indicate that the quantity of protein expressed is directly related to the amount of DNA delivered during injection.

EXAMPLE 9

In ovo Injection of β-Galactosidase Construct

The plasmid pmiwz was prepared by the method described in Example 2. This preparation was injected manually into breast, pipping, or thigh muscle tissue of day 18 or day 19 chick embryos. A 26 gauge, ⅜ inch needle was used for delivery. The dosage was varied between 0, 25 and 50 µg of plasmid in 100 µL of delivery vehicle. The aperture created by the needle was sealed with polyethylene film.

Birds were hatched and euthanized with $CO_2$. Muscle samples were prepared and analyzed by PCR through the procedure described in Example 3.

EXAMPLE 10

Results of PCR Assay for DmiwZ Injected into Day 18 and Day 19 Chick Embryos The results of the PCR analysis of Example 10 are shown in Table 4 below. Samples were taken only from birds upon which the injection site could be detected.

TABLE 4

| Persistence of In Ovo Injected pmiwZ (50 µg) at hatch | | |
|---|---|---|
| Injection date | Day 18 embryos | Day 19 embryos |
| Total Birds Tested | 8 | 6 |
| Positive Samples | 7 | 6 |

These data indicate that a DNA construct injected into muscle tissue in ovo can persist in the muscle tissue to hatch. This finding suggests that muscle tissue can be used as the injection site for DNA constructs which will produce exogenous proteins, and thus intramuscular injection is a viable method for introducing foreign DNA into birds.

EXAMPLE 11

Muscle Injection In Ovo

These experiments were conducted to evaluate injection methods for their ability to target embryonic muscle.

I. Injection into breast region at 1" to 1½" (2.5 –3.8 cm) Depth.

This experiment determined whether injections at depths of 1"–1.5" (2.5–3.8 cm) reached into the breast region of chick embryos. Day 18 or 19 embryonated broiler eggs were injected with India ink, 100 µL in each egg, at various depths. Eggs were injected through the top (large end). All injections were made utilizing automated single egg injection. No attempt was made to orient the eggs with respect to the position of the embryo within the egg. Eggs were then broken open and examined visually to determine specifically where the dye was injected.

Results are shown in Table 5. The dye was injected into the breast region from 3 to 67% of the time, depending on the depth of injection used.

TABLE 5

| Injection of Day 18 and Day 19 Eggs | | | | |
|---|---|---|---|---|
| Day of Incubation | Injection Depth | Breast Region % | Other % | Eggs Examined |
| 18 | 1½" (3.8 cm) | 34 | 66 | 27 |
| 19 | 1½" (3.8 cm) | 16 | 84 | 49 |
| 18 | 1" (2.5 cm) | 36 | 64 | 35 |
| 19 | 1" (2.5 cm) | 33 | 67 | 28 |
| 18 | 1¼" (3.7 cm) | 67+ | 33 | 33 |
| 19 | 1⅛" (2.8 cm) | 3 | 97 | 30 |

II. Injection Into Breast Muscle Tissue—1½" (3.8 cm) Depth.

Forty-nine day 19 embryonated broiler eggs were injected at 1½" (3.8 cm) depth with 50 µL of India ink each, using a single egg injector. Eggs were then broken open and examined visually to determine specifically where the dye was injected. The embryo was found to be injected in 88% of eggs, and 16% of the injections entered breast muscle tissue. Results are shown in Table 6.

TABLE 6

| Injection of Day 19 Eggs 1½" (3.8 cm) Depth | | | | | | | |
|---|---|---|---|---|---|---|---|
| Eggs Examined | Neck | Throat | Breast Muscle | Breast and Internal | Lung or Body Cavity | Yolk Sac | Amnion |
| 49 | 8% | 5% | 12% | 4% | 56% | 2% | 12% |

III. Injection Into Breast Muscle Tissue (⅞" Depth).

Day 19 embryonated broiler eggs were injected manually with 50 µL of India ink at a depth of ⅞" (2.2 cm) directly through the center of the axis. As above, eggs were broken open and examined to determine whether the needle traversed breast muscle tissue. An initial experiment found 42.7% of the injections landed directly in the breast muscle while 35% landed subcutaneously on top of the breast muscle (Table 7).

To insure the lack of injection accuracy was not due to poor incubation conditions, the experiment described above was replicated at a second hatchery. Results were similar. (Data not shown).

TABLE 7

Injection of Day 19 Eggs -- ⅞" (2.2 cm) Depth

| Eggs Examined | Breast Muscle | Sub-cutaneous | Internal | Amnion |
|---|---|---|---|---|
| 68 | 42.7% | 35.3% | 10.0% | 12% |

IV. Developmental Variation and Injection Accuracy

The aircell depth of Day 18 and 19 embryonated broiler eggs was determined to ascertain the developmental variability and the relationship of this variable to injection accuracy. The aircell depth decreases as the embryo grows and reorients into a pipping position. Automated egg injection was then used to inject 120 eggs through the top (large end) of the egg at a depth of ⅞" (2.2 cm) with 50 μL of India ink. Results are shown in Table 8. 89% of the eggs had an aircell depth of 3–6 mm; the injection accuracy was slightly higher when the aircell depth was 4–5 mm. The percentage of injections placed directly into the breast muscle was only 31%.

TABLE 8

Variation and Effect of Aircell Depth of Day 19 Broiler Eggs on Injection Into the Breast Muscle

| Aircell Depth (mm) | 2 | 3 | 4 | 5 | 6 | 7 | 8 | 9 |
|---|---|---|---|---|---|---|---|---|
| Distribution % | 3 | 29 | 27 | 18 | 13 | 2 | 5 | 1 |
| Pipping % | 50 | 37 | 6 | 5 | 0 | 0 | 0 | 0 |
| Breast Muscle % | 25 | 20 | 47 | 36 | 19 | 0 | 33 | 100 |

V. Injection of Day 19 Eggs at ⅞" (2.2 cm) Depth

Two trials of 60 day 19 embryonated broiler eggs were carried out, with injection through the top (large end) at a depth of ⅞" (2.2 cm). It was determined that the injections did not always directly hit the breast muscle, but often first hit the back or shoulder of the embryo and traversed the body cavity to exit into or through the right pectoral. At least 60% of the injections (those indicated as breast and subcutaneous) penetrated muscle tissue at some point. Results are shown in Table 9.

Additionally many of the internal injections were in the lungs or intercostal ribs directly underneath the breast muscle.

TABLE 9

Dye Placement Following Injection ⅞" (2.2 cm) Through the Top of Day 19 Broiler Eggs

| | Eggs Examined | Breast Muscle | Subcutaneous | Internal | Amnion | Embryo |
|---|---|---|---|---|---|---|
| Trial 1 | 60 | 36 | 22 | 34 | 3 | 97 |
| Trial 2 | 60 | 27 | 15 | 37 | 3 | 97 |
| Average | 120 | 31 | 29 | 36 | 3 | 97 |

V. Injection at Increased Depth

An experiment was performed wherein the injection depth was increased so that all injections would exit through the breast, and wherein India ink was injected as the needle was withdrawn (to leave a trail of the substance injected). This determined whether the needle's path traversed muscle cells.

Needles were inserted into eggs and the eggs broken open with the needle in place to visualize if and how the needle had penetrated the muscle tissue. Numerous observations utilizing this technique led to the following conclusions. The needle path depends partly upon either the developmental stage of the embryo or upon variation of each individual embryo's position within the egg. As the embryo nears pipping, his head moves further underneath the wing toward the eggshell, causing his back to roll toward the center of the egg. When in this position, a needle entering the top center of the egg will enter the back or shoulder of the embryo and traverse the body cavity sometimes ending either in the breast muscle or exiting the muscle tissue to land subcutaneously on top of the breast muscle. Other times the needle will traverse the body cavity but never enter the breast muscle tissue, landing in the chest or abdominal cavity. When the embryo is centered around the axis the needle enters between the wing and the chest either penetrating breast muscle, skimming the breast and landing directly underneath the skin (but not penetrating muscle tissue) or entirely missing the breast and ending in the amnion or entering the abdominal region. If the needle does not enter the center of the egg, the injection can end in the throat or neck of the embryo.

EXAMPLE 12

Angled Injection Through the Top of the Egg for Breast Muscle Targetting

Angling the injection needle toward or into the breast muscle was investigated to determine whether this would prevent the needle from skimming across the top of the breast muscle (resulting in subcutaneous injection). This technology requires first orienting the embryo relative to the needle's path. Experiments were conducted to determine if this technique would increase the percentage of injections made directly into the muscle tissue.

The best angle for injection was determined by candling eggs and marking the highest part of the aircell or the shoulder. Needles were directed toward the shoulder or breast of the embryo before injection. Needles directed at an angle of 5 degrees landed at a frequency of 60% on the upper tip of the breast. An angle of 2.5% hit 7 of 9 (78%) embryos tested in the breast muscle, one in the throat and one on top of the breast or subcutaneously. An angle of 2.5% was utilized in all future studies.

A study utilized 50 μL India ink injection and compared angled to perpendicular injections. Results are shown in Table 10. The angled injection increased the frequency of contacting muscle tissue by 40%. In a second study investigating muscle injection using the fixed needle technique, the perpendicular technique penetrated muscle at some point in 54% of the eggs tested (n=21), while the angled approach traversed muscle tissue in 90% (n=22). A subsequent study of the angled approach utilizing 108 eggs demonstrated an injection accuracy of 92%. A summary of all experiments conducted utilizing the angled approach suggest that muscle tissue is penetrated with a 93% accuracy by this technique (Table 11).

TABLE 10

Perpendicular vs. Angled Injection Technique

| Technique | Eggs Examined | Breast Muscle | Sub-cutaneous | Abdominal or Amnion |
|---|---|---|---|---|
| Perpendicular | 18 | 33% | 39% | 28% |
| Angled | 24 | 71% | 21% | 8% |

TABLE 11

Summary of Angled Injection Trials

| Trial | Breast Muscle Hits | Eggs Examined | % |
|---|---|---|---|
| 1 | 17 | 24 | 71% |
| 2 | 99 | 108 | 92% |
| 3 | 19 | 21 | 90% |
| 4 | 7 | 9 | 78% |
| 5 | 15 | 17 | 88% |

The foregoing examples are illustrative of the present invention, and are not to be construed as limiting thereof. The invention is defined by the following claims, with equivalents of the claims to be included therein.

That which is claimed is:

1. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding a protein operably linked to a promoter;

maintaining said chicken embryo in ovo throughout said incubation; and hatching said chicken, wherein said protein is expressed in said chicken after hatch to detectable levels.

2. The method according to claim 1, wherein said DNA is a vector.

3. The method according to claim 1, wherein said DNA is coupled with a liposome.

4. The method according to claim 1, wherein said protein is selected from the group consisting of growth hormone, insulin-like growth factor, lymphokines, epidermal growth factor, and thyroid releasing hormone.

5. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding an immunogenic protein operably linked to a promoter;

maintaining said chicken embryo in ovo throughout said incubation; and hatching said chicken, wherein said immunogenic protein is expressed in said chicken after hatch to detectable levels.

6. The method according to claim 5, wherein said DNA is a vector.

7. The method according to claim 5, wherein said DNA is coupled with a liposome.

8. A method of delivering DNA to a chicken, comprising;

(a) obtaining a chicken egg containing a 17–19 day chicken embryo;

(b) injecting DNA into the shoulder muscle tissue or breast muscle tissue of said chicken embryo, wherein said DNA comprises a nucleic acid sequence encoding a protein operably linked to a promoter;

wherein said injecting comprises:

i) positioning an elongate injection needle at the large end of the egg at an angle offset about 1 to 5 degrees from the long axis of said egg, said angle selected so that the needle is directed toward the shoulder or breast of said embryo;

ii) inserting said needle through the shell of said egg along an essentially linear path of travel to a depth of about ⅞ inch to 1.5 inch into the shoulder or breast of said embryo; and (c) hatching said chicken, wherein said protein is expressed in said chicken after hatch to detectable levels.

9. The method according to claim 8, wherein said DNA is a vector selected from the group consisting of a plasmid vector, viral vector, and phage vector.

10. The method according to claim 8, wherein said DNA is a plasmid vector.

11. A method of delivering DNA to a chicken, comprising:

(a) obtaining a chicken egg containing a 17–19 day chicken embryo;

(b) injecting DNA into the shoulder muscle tissue or breast muscle tissue of said chicken embryo, wherein said DNA comprises a nucleic acid sequence encoding an immunogenic protein operably linked to a promoter;

wherein said injecting comprises:

i) positioning an elongate injection needle at the large end of the egg at an angle offset about 1 to 5 degrees from the long axis of said egg, said angle selected so that the needle is directed toward the shoulder or breast of said embryo;

ii) inserting said needle through the shell of said egg along an essentially linear path of travel to a depth of about ⅞ inch to 1.5 inch into the shoulder or breast of said embryo; and (c) hatching said chicken, wherein said immunogenic protein is expressed in said chicken after hatch to detectable levels.

12. The method according to claim 11, wherein said DNA is a vector selected from the group consisting of a plasmid vector, viral vector, and phage vector.

13. The method according to claim 8, wherein said DNA is a plasmid vector.

14. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding a protein operably linked to a promoter and wherein said DNA is a vector selected from the group consisting of a plasmid vector, a viral vector, and a phage vector;

maintaining said chicken embryo in ovo throughout said incubation; and hatching said chicken, wherein said protein is expressed in said chicken after hatch to detectable levels.

15. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding an immunogenic protein operably linked to a promoter and wherein said DNA is a vector selected from the group consisting of a plasmid vector, a viral vector, and a phage vector;

maintaining said chicken embryo in ovo throughout said incubation; and hatching said chicken, wherein said immunogenic protein is expressed in said chicken after hatch to detectable levels.

16. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding a protein operably linked to a promoter and wherein said DNA is a plasmid vector;

maintaining said chicken embryo in ovo throughout said incubation; and hatching said chicken, wherein said protein is expressed in said chicken after hatch to detectable levels.

17. A method of delivering DNA to a chicken comprising:

injecting DNA in an aqueous, pharmaceutically-acceptable carrier into the muscle tissue of a chicken embryo in ovo during the last quarter of in ovo incubation, wherein said DNA comprises a nucleic acid sequence encoding an immunogenic protein operably linked to a promoter and wherein said DNA is a plasmid vector;

maintaining said chicken embryo in ovo throughout said incubation; and hatching said chicken, wherein said immunogenic protein is expressed in said chicken after hatch to detectable levels.

18. A method of delivering DNA to a chicken comprising:

injecting DNA into the muscle tissue of a chicken embryo in ovo during the last quarter of in ovo incubation, wherein said DNA comprises a nucleic acid sequence encoding a protein operably linked to a promoter and wherein said muscle tissue is selected from the group consisting of breast muscle tissue, pipping muscle tissue, and shoulder muscle tissue;

maintaining said chicken embryo in ovo throughout said incubation; and hatching said chicken, wherein said protein is expressed in said chicken after hatch to detectable levels.

19. A method of delivering DNA to a chicken comprising:

injecting DNA into the muscle tissue of a chicken embryo in ovo during the last quarter of in ovo incubation, wherein said DNA comprises a nucleic acid sequence encoding an immunogenic protein operably linked to a promoter and wherein said muscle tissue is selected from the group consisting of breast muscle tissue, pipping muscle tissue, and shoulder muscle tissue;

maintaining said chicken embryo in ovo throughout said incubation; and hatching said chicken, wherein said immunogenic protein is expressed in said chicken after hatch to detectable levels.

* * * * *